United States Patent [19]

Wyatt

[11] 4,419,345

[45] Dec. 6, 1983

[54] SLEEP-INDUCING PHARMACEUTICAL COMPOSITION AND METHOD

[75] Inventor: Richard J. Wyatt, Bethesda, Md.

[73] Assignee: Kinetic Systems, Inc., Arlington, Va.

[21] Appl. No.: 284,684

[22] Filed: Jul. 20, 1981

[51] Int. Cl.$^3$ .................. A61K 31/195; A61K 33/06; A61K 33/14

[52] U.S. Cl. .................................. 424/153; 424/154; 424/319

[58] Field of Search ........................ 424/319, 153, 154

[56] References Cited

U.S. PATENT DOCUMENTS

| | | | |
|---|---|---|---|
| 2,766,255 | 10/1956 | Westfield et al. | 424/274 |
| 3,026,325 | 3/1962 | Heinzelman et al. | 424/274 |
| 3,847,941 | 11/1974 | Brana et al. | 260/326.14 |
| 4,000,297 | 12/1976 | Rovati et al. | 424/274 |
| 4,029,807 | 6/1977 | Roldan et al. | 424/274 |
| 4,161,530 | 7/1979 | Koella | 424/274 |

OTHER PUBLICATIONS

John A. Oates, M.D. et al., "Neurologic Effects of Tryptophan in Patients Receiving a Monoamine Oxidase Inhibitor", pp. 1076-1078.
Richard J. Wyatt et al., "Effects of L-Tryptophan (A Natural Sedative) on Human Sleep," Oct. 24, 1970, pp. 842-846.
B. J. Key et al., "Neuropharmacological Comparison of Cystathionine, Cysteine, Homoserine and Alpha-Ketobutyric Acid in Cats, 38 1970, pp. 349-357.
J. Hubert Lacey et al., "The Immediate Effect of Intravenous Specific Nutrients on EEG Sleep," 1978, pp. 275-280.
Ernest Hartmann, M.D., "Brief Communication-Sleep Induced by L-Tryptophan," vol. 167, No. 8, pp. 497-499.
Nathaniel Kleitman, "Sleep and Wakefulness," pp. 200-202.
Carlton K. Erickson et al., "Ethanol: Modification of Acute Intoxication by Divalent Cations," Mar. 17, 1978, pp. 1219-1221.
R. Adron Harris, "Alteration of Alcohol Effects by Calcium and Other Inorganic Cations," 1979, pp. 527-534.
P. T. Männistö, "Effect of Lithium and Rubidium on the Sleeping Time Caused by Various Intravenous Anaesthetics in the Mouse," 1976, pp. 185-189.
John Scott Carman et al., "Calcium: Bivalent Cation in the Bivalent Psychoses," 1979, pp. 295-336.
"Cuisine"-The Magazine of Food and Creative Living, May 1979, 2 pp.

*Primary Examiner*—Stanley J. Friedman
*Attorney, Agent, or Firm*—Finnegan, Henderson, Farabow, Garrett & Dunner

[57] ABSTRACT

A highly effective sleep-inducing pharmaceutical composition that causes few, if any, side-effects contains an amino acid and a cation in certain proportions. The amino acid may be tryptophan, cystathionine, or lysine, preferably tryptophan, and most preferably L-tryptophan, and the cation may be calcium, magnesium, manganese, or lithium, preferably calcium or magnesium, and most preferably calcium. The ratio of amino acid to cation is about 0.02:1 to 1.0:1 when the cation is calcium or magnesium, 5:1 to 100:1 when the cation is manganese, and 0.02:1 to 100:1 when the cation is lithium. The pharmaceutical composition may be administered in any conventional manner.

8 Claims, No Drawings

SLEEP-INDUCING PHARMACEUTICAL COMPOSITION AND METHOD

BACKGROUND OF THE INVENTION

The present invention relates to a sleep-inducing pharmaceutical composition and a method of inducing sleep that is highly effective, but causes few, if any, side-effects. There has long been a need for such a sedative, because the sedatives presently available either are not effective enough or cause significant side-effects.

It is known that the amino acid L-tryptophan possesses sedative qualities (Oates and Sjoerdsma, Neurology 10: 1076–1078, 1960), and in 1970 (Wyatt et al, Lancet 842–46) it was suggested that L-tryptophan might be used as a natural sedative. Other amino acids may also affect sleep: cystathionine induces a sleeplike EEG in cats (Key and White, Neuropharmacology 9: 349–57, 1970); L-lysine (Chang et al, Life Sciences 28: 407–13, 1981) and amino acid mixtures given intravenously to humans enhance non-REM sleep (Lacey et al, Electroenceph. Clin. Neurophysiol. 44: 275–80, 1978).

L-tryptophan has not, however, been widely used as a sedative, probably because of the large quantity (bulk) of L-tryptophan that is needed to induce sleep. Thus, the smallest quantity that has been found to successfully initate sleep is one gram. Hartman and Spinweber (J. of Nervous and Mental Disease, 167: 4, 497–99, 1979) found that one gram of L-trytophan decreased sleep latency in normal men by about 50 percent. One-half agram had no effect.

One way to reduce the quantity (bulk) of L-tryptophan needed to induce sleep would be to combine it with another active substance. Such an approach is suggested by Koella (U.S. Pat. No. 4,161,530), who discloses combining L-tryptophan with beta-receptor-blocking compounds. The principal disadvantage of this approach is that there is no evidence that the effects are more than additive and that the addition of the beta-receptor-blocking compounds does not detract from the endogenous qualities of tryptophan. The beta-receptor-blockers are not naturally present in humans and are likely to have unknown, but significant side-effects.

It has been known, however, that there are other naturally occurring substances that produce sedation. The cations, magnesium and calcium, when injected directly into the brains of animals produce sedation. Kleitman, Sleep and Wakefulness 200–02 (1939). Erickson et al (Science 199: 1219–21, 1978) have found that when the cations magnesium, calcium, or cadmium are injected directly into the brains of mice they potentiate the sedative effects of ethanol. Similarly, peripheral injections of manganese (Harris, Pharmacol. Biochem. Behav. 10: 527–34, 1979) and beryllium (Ribeiro, Proc. West. Pharmac. Soc. 13:13, 1970) potentiate ethanol-induced sedation, and rubidium may enhance diazepam-induced sleeping time (Mannisto and Saarnivaara, Brit. J. Anaes. 48: 185–89, 1976). Calcium when given orally by itself is known to have mild sedative properties in humans (Carman and Wyatt, Biological Psych. 14: 295–336, 1979).

SUMMARY OF THE INVENTION

In accordance with the present invention, when tryptophan, cystathionine, or lysine and a cation selected from the group consisting of calcium, magnesium, manganese, and lithium are administered simultaneously and in certain proportions, they decrease sleep latency and enhance total sleep at dosages of these substances that by themselves have little or no effect. Of particular interest, this synergistic enhancement of sleep takes place at dosages of the substances that are within the normal daily dietary intake and therefore occurs without side-effects.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the pharmaceutical composition of the invention for inducing sleep comprises a sleep-inducing effective amount of a combination of an amino acid selected from the group consisting of tryptophan, cystathionine, and lysine or a non-toxic salt thereof and a cation selected from the group consisting of calcium, magnesium, manganese, and lithium, wherein the weight ratio of the amino acid or a non-toxic salt thereof to the cation is about 0.02:1 to 1.0:1 when the cation is calcium or magnesium, 5:1 to 100:1 when the cation is manganese, and 0.02:1 to 100:1 when the cation is lithium. The amino acid is preferably in the L form, but the D form or a racemic mixture may also be used.

Further to achieve the foregoing objects and in accordance with the purpose of the invention, as embodied and broadly described herein, the method of the invention for inducing sleep in warm blooded animals comprises the administration thereto of a sleep-inducing effective amount of a combination of an amino acid selected from the group consisting of tryptophan, cystathionine, and lysine, or a non-toxic salt thereof and a cation selected from the group consisting of calcium, magnesium, manganese, and lithium, wherein the ratio of the amino acid or a non-toxic salt thereof to the cation is as described above with respect to the composition. Again, the L form of the amino acid is preferred.

DESCRIPTION OF THE PREFERRED EMBODIMENTS

Reference will now be made in detail to the presently preferred embodiments of the invention.

In accordance with the invention, the amino acid may be tryptophan, cystathionine, or lysine, or a non-toxic salt thereof. The preferred amino acid is tryptophan, most preferably L-tryptophan. Non-toxic salts of the amino acid that may be used are those that can be used pharmaceutically, including acid addition salts with strong acids, especially with strong inorganic acids, for example hydrochloric, sulfuric, or phosphoric acids, or with strong organic acids, especially sulfonic acids, for example methane sulfonic acid, and also salts with strong bases, especially the alkali metal salts or alkaline earth metal salts, for example sodium salts or potassium salts.

The cation in accordance with the invention may be selected from the group consisting of calcium, magnesium, manganese, and lithium. The cation may be present in the form of a non-toxic salt, such as a chloride, gluconate, lactate, dibasic phosphate, sulfate, citrate, gluceptate, carbonate, or levulinate. Or the cation may be totally or partially chemically bound to the amino acid. The preferred cations are calcium and magnesium, especially calcium.

The weight ratio of amino acid or a non-toxic salt thereof to cation to obtain the surprising potentiation of the invention varies with the particular cation. The Table sets forth a broad weight ratio range of amino acid to cation and preferred ranges for each cation.

TABLE

| Element | Broad | Preferred | Most Preferred |
|---------|-------|-----------|----------------|
| Ca | 0.02:1–1:1 | 0.17:1–1:1 | 0.50:1–0.84:1 |
| Mg | 0.02:1–1:1 | 0.17:1–1:1 | 0.64:1–0.84:1 |
| Mn | 5:1–100:1 | 17:1–100:1 | 64:1–84:1 |
| Li | 0.02:1–100:1 | 0.17:1–12:1 | 0.33:1–0.66:1 |

The absolute dosage of the active components in the pharmaceutical composition of the present invention varies greatly and depends on the activity of the components used. In general, the compositions for use in humans should contain from about 20 milligrams to 1 gram of amino acid, preferably from about 100 milligrams to 1 gram of amino acid, most preferably about 350 to 400 milligrams. Preferred amounts of calcium and magnesium are between about 400 and 600 milligrams, most preferably about 500 milligrams. Preferred amounts of manganese are about 1 to 10, more preferably 4 to 6, milligrams. Preferred amounts of lithium are about 30 to 150 milligrams and most preferably 100 to 150 milligrams.

In addition to the amino acid and the cation of the present invention, the composition may contain suitable excipients and auxiliaries that facilitate processing of the active compounds into preparations that can be used pharmaceutically. Preferably the preparations, above all preparations that can be administered orally and can be used for the preferred type of administration, such as tablets, dragees, and capsules, and also preparations that can be administered rectally, such as suppositories, as well as suitable solutions for administration by injection or orally, contain from about 20% to 100%, preferably from about 50% to about 90%, of active compounds together with the excipient.

The pharmaceutical preparations of the present invention are manufactured in a manner that is in itself known, for example by means of conventional mixing, granulating, dragee-making, dissolving, or lyophilising processes. Thus, pharmaceutical preparations for oral use can be obtained by combining the active compounds with solid excipients, optionally granulating a resulting mixture and processing the mixture of granules, after adding suitable auxiliaries if desired or necessary, to give the tablets or dragee cores.

Suitable excipients are, in particular, fillers, such as sugars, for example lactose or sucrose, mannitol or sorbitol, cellulose preparations and/or calcium phosphates, for example tricalcium phosphate or calcium hydrogen phosphate, as well as binders, such as starch pastes using, for example, maize starch, wheat starch, rice starch or potato starch, gelatine tragacanth, methylcellulose, hydroxypropylmethylcellulose, sodium carboxymethylcellulose and/or polyvinylpyrrolidone, and/or, if desired, disintegrating agents, such as the abovementioned starches, and also carboxymethyl-starch, cross-linked polyvinylpyrrolidone, agar or alginic acid or a salt thereof, such as sodium alginate. Auxiliaries are, above all, flow-regulating agents and lubricants, for example silica, talc, stearic acid or salts thereof, such as magnesium stearate are provided with suitable coatings, which, if desired, are resistant to gastric juices, and for this purpose, inter alia, concentrated sugar solutions, which optionally contain gum arabic, talc, polyvinylpyrrolidone, polyethylene glycol and/or titanium dioxide, lacquer solutions in suitable organic solvents or solvent mixtures or, in order to produce coatings resistant to gastric juices, solutions of suitable cellulose preparations, such as acetylcellulose phthalate or hydroxypropylmethylcellulose phthalate, are used. Dyestuffs or pigments can be added to the tablets or dragee coatings, for example for identification or in order to characterize different combinations of active compound doses.

Other pharmaceutical preparations that can be used orally are push-fit capsules made of gelatine, as well as soft, sealed capsules made of gelatine and a plasticiser, such as glycerol or sorbitol. The push-fit capsules can contain the active compounds in the form of granules, for example mixed with fillers, such as lactose, binders, such as starches, and/or lubricants, such as talc or magnesium stearate, and, optionally, stabilizers. In soft capsules, the active compounds are preferably dissolved or suspended in suitable liquids, such as fatty oils, liquid paraffin or liquid polyethylene glycols, it also being possible to add stabilizers.

Possible pharmaceutical preparations which can be used rectally are, for example, suppositories, which consist of a combination of the active compounds with a suppository base. Suitable suppository bases are, for example, natural or synthetic triglycerides, paraffin hydrocarbons, polyethylene glycols or higher alkanols. In addition it is also possible to use gelatine rectal capsules that consist of a combination of the active compounds with a base; possible base materials are, for example, liquid triglycerides, polyethylene glycols or paraffin hydrocarbons.

Suitable formulations for parenteral administration are, above all, aqueous solutions of the active compounds in a water-soluble form, for example in the form of water-soluble salts, and also suspensions of the active compounds, such as appropriate oily injection suspensions, for which suitable lipophilic solvents or vehicles, such as fatty oils, for example sesame oil, or synthetic fatty acid esters, for example ethyl oleate or triglycerides, are used, or aqueous injection suspensions that contain substances that increase the viscosity, for example sodium carboxymethylcellulose, sorbitol and/or dextran, and optionally also contain stabilizers.

The following example illustrates the potentiation that is achieved with the present invention, but is not intended to restrict the scope of the invention in any way.

EXAMPLE

This example was designed and carried out to demonstrate the effects of L-tryptophan and calcium alone and in combination, on the sleep EEG of the rat. The animals were 250–275 gram male Sprague-Dawley rats, in whom stainless steel screw cortical EEG electrodes and stainless-steel nuchal EMG electrodes had been surgically implanted at least one week before recording. The recordings, of one hour duration, were performed at 8:00 p.m. with the lights on, using a polygraph calibrated to 50 $\mu$V/10 mm. and a paper speed of 10 mm/sec. Sleep stages were determined in 30 second epochs according to standard criteria: waking=low amplitude, mixed frequency EEG and high EMG; non REM sleep=high amplitude, low frequency EEG and low amplitude EMG. W. B. Mendelson et al, Pharmacology Biochemistry and Behavior 2: 553-56, 1974. The two parameters tabulated were sleep latency (time from the beginning of recording to sleep onset defined as a least one continuous minute of sleep) and total sleep (total time of non REM and REM sleep). Statistical significance was assessed by a one-way analysis of variance. The four independent treatment groups were given intraperitoneally 1) saline placebo; 2) 36 mg/kg of L-tryptophan; 3) 2 millimoles/kg of calcium chloride; and 4) 36 mg/kg L-tryptophan plus 2 mm/kg calcium chloride. The results were as follows (Mean±(SEM), minutes):

| Treatment | Sleep Latency | Total Sleep |
|---|---|---|
| Placebo(n = 8) | 21.1(5.1) | 9.1(1.4) |
| L-tryptophan plus placebo(n = 9) | 24.9(7.2) | 9.6(2.6) |
| Calcium plus placebo(n = 18) | 15.0(3.3) | 10.6(1.5) |
| Calcium plus L-tryptophan(n = 13) | 6.8(1.8) | 15.1(1.8) |
| n = number of animals | | |
| Df = degrees of freedom | | |
| F = ratio of variances | | |
| | $F = 3.3215$ | $F = 2.0799$ |
| | $Df = 3,44$ | $Df = 3,44$ |
| Two tailed | $p < 0.027$ | $p < 0.115$ |
| One tailed | | $p < 0.071$ |

These data demonstrate that the two compounds when administered alone have little effect on sleep latency or total sleep, but significantly induce and maintain sleep when given in combination.

It will be apparent to those skilled in the art that various modifications and variations could be made in the composition and method of the invention without departing from the scope or spirit of the invention.

What is claimed is:

1. A pharmaceutical composition for inducing sleep, comprising a sleep-inducing effective amount of a combination of tryptophan or a non-toxic salt thereof and a calcium cation, wherein the weight ratio of the tryptophan or a non-toxic salt thereof to the cation is about 0.02:1 to 1.0:1.

2. A pharmaceutical composition according to claim 1, wherein said amino acid is L-tryptophan.

3. A pharmaceutical composition according to claim 2, wherein the ratio of tryptophan to calcium is 0.17:1 to 1.0:1.

4. A pharmaceutical composition according to claim 3, wherein said ratio is between 0.50:1 and 0.84:1.

5. A method for inducing sleep in warm blooded animals, comprising administering thereto a sleep-inducing effective amount of a combination of tryptophan, or a non-toxic salt thereof and a calcium cation wherein the weight ratio of the tryptophan or a non-toxic salt thereof to the cation is about 0.02:1 to 1.0:1.

6. A method according to claim 5, wherein said amino acid is L-tryptophan.

7. A method according to claim 6, wherein the ratio of L-tryptophan to calcium is 0.17:1 to 1.0:1.

8. A method according to claim 7, wherein said ratio is between 0.50:1 and 0.84:1.

* * * * *